United States Patent [19]

Lines et al.

[11] 3,953,362

[45] Apr. 27, 1976

[54] MOLYBDENUM SALT CATALYSTS AND METHODS OF PREPARING THEM

[75] Inventors: Ellwood L. Lines, Westville; John A. Herbst, Madison; Robert J. Fairbrother, Wallingford, all of Conn.

[73] Assignee: Olin Corporation, New Haven, Conn.

[22] Filed: Apr. 30, 1975

[21] Appl. No.: 573,293

[52] U.S. Cl. .................... 252/431 N; 260/348.5 R
[51] Int. Cl.² ........................................ B01J 31/12
[58] Field of Search ...................... 252/431 N, 467; 260/429 R

[56] References Cited

UNITED STATES PATENTS 3,434,975    3/1969    Sheng et al. .................... 252/467 X

*Primary Examiner*—W. J. Shine
*Attorney, Agent, or Firm*—Kenneth P. Glynn

[57] ABSTRACT

Novel molybdenum salt catalysts and a method of preparing them are described. The catalysts, which are useful in epoxidation reactions, are prepared by reacting an oxygen-containing molybdenum compound, hydrogen peroxide and an amine, and optionally water or an alkylene glycol, at elevated temperatures.

32 Claims, No Drawings

MOLYBDENUM SALT CATALYSTS AND METHODS OF PREPARING THEM

The present invention is directed to novel compositions and to the method of making these compositions. More particularly, the present invention is directed to novel molybdenum salt catalysts which are prepared by reacting an oxygen-containing molybdenum compound with hydrogen peroxide and an amine.

The molybdenum salt catalysts of the present invention are useful in preparing a variety of commercially important organic epoxide compounds, such as alkylene epoxides. These catalysts are particularly useful in catalysis of the epoxidation reaction of unsaturated organic compounds with peroxidic compounds such as hydrogen peroxide. Thus, the highly soluble molybdenum salt catalysts of the present invention may be employed in the preparation of widely used alkylene oxide commodities, such as propylene oxide, by indirect oxidation of alkylene starting materials.

The molybdenum salt catalysts of the present invention are reaction products resulting from the reaction of an oxygen-containing molybdenum compound, hydrogen peroxide and an amine. The oxygen-containing molybdenum compound may be, for example, the ammonium salt of molybdic acid, or it may be one containing only oxygen and molybdenum atoms, e.g., molybdenum dioxide, molybdenum sesquioxide, molybdenum trioxide or mixtures of these, and the preferred molybdenum starting material is molybdenum trioxide.

The hydrogen peroxide sarting material may be commercial grade $H_2O_2$ or may be crude peroxide (i.e. containing a minor amount of organic peroxides) and is generally used in an organic solvent solution. The organic solvent used is one which is compatible with and inert to all of the reactants involved. The alcohols, and preferably the secondary alcohols, such as isopropanol and sec-butanol, are especially suitable for this purpose. When isopropanol is employed as the solvent, it is particularly advantageous to use crude hydrogen peroxide in isopropanol obtained by oxidizing isopropanol with oxygen and removing, at least partially, the acetone by-product.

The amine starting material employed in the preparation of the novel catalysts of the present invention is a compound having the formula $R_1R_2R_3N$ wherein $R_1$, $R_2$, and $R_3$ are each independently selected from hydrogen, substituted and unsubstituted alkyls having about 1 to about 10 carbon atoms, preferably about 1 to about 6 carbon atoms, and substituted and unsubstituted aryls having about 6 to about 10 carbon atoms, preferably about 6 to 8 carbon atoms, with the proviso that at least one of $R_1$, $R_2$, and $R_3$ is not hydrogen. Thus primary, secondary and tertiary amines may be used, although the tertiary amines are preferred. Additionally, the amine starting materials used to produce the molybdenum salt catalysts of the present invention include the N-oxides of the tertiary amine compounds of the above formula. Preferred among the amine starting materials are tertiary amines wherein $R_1$, $R_2$, and $R_3$ are each independently methyl, ethyl or butyl, and the N-oxides of these.

In the method of making the molybdenum salt catalysts of the present invention, the oxygen-containing molybdenum compound, the hydrogen peroxide and the amine are combined and reacted at elevated temperatures. Generally, about 0.1 to about 4 moles of hydrogen peroxide and preferably about 0.5 to about 2 moles of hydrogen peroxide are used per mole of molybdenum. About 0.1 moles to about 4 moles of the amine, and preferably about 0.3 to about 2 moles of the amine are employed per mole of molybdenum. The reactants are combined with the oxygen-containing molybdenum compound in any order and heated to a temperature to effect reflux. For example, a temperature of about 60°C. to about 100°C. and preferably a temperature of about 70°C. to about 85°C. may be used depending upon the particular reactants and solvent employed.

The oxygen-containing molybdenum compound, the $H_2O_2$ and the amine react to produce a molybdenum salt catalyst and the reaction may be run for about 30 minutes or even less to about 12 hours or more depending upon the reactants and the reaction temperature chosen, but generally the reaction is completed to a satisfactory degree in about 1.5 hours to about 3 hours.

The novel catalysts obtained by the method of the present invention are believed to be molybdenum salts having anions comprising molybdenum and oxygen, and perhaps hydrogen, e.g., in hydroxyl groups and having cations comprising ammonium radicals derived from amine starting materials. However, the novel catalysts of the present invention are the reaction products of the above-mentioned starting materials and the concept that they contain Mo,O and perhaps OH based anions and ammonium cations is theoretical speculation, and the novel catalysts should not be construed to be limited thereto.

While the catalysts prepared by the method of the present invention have as essential starting materials oxygen-containing molybdenum compounds, hydrogen peroxide and amines, additional starting materials may be included without exceeding the scope of the present invention.

For example, in addition to the three essential starting materials mentioned, water may be included as a reactant. In this case, about 0.1 to about 4 moles of hydrogen peroxide, and preferably about 0.5 to about 2 moles of hydrogen peroxide, per mole of molybenum is used in combination with about 1 to about 50 moles of water, and preferably about 10 to about 20 moles of water per mole of molybdenum. No change in the amount of amine starting material per mole of molybdenum is necessary.

Alternatively, an alkylene glycol, especially the lower alkylene glycols having about 2 to aout 6, and preferably about 3 to about 4 carbon atoms, may be incuded as a starting material with the essential materials and reacted therewith to obtain novel molybdenum catalysts of the present invention. In this embodiment about 0.1 to about 4 moles of $H_2O_2$ and preferably about 0.5 to about 2 moles of $H_2O_2$ per mole of molybdenum is used in combination with about 0.1 to about 4, and preferably about 0.5 to about 2 moles of alkylene glycol per mole of molybdenum. In this embodiment, the amount of amine starting material is the same as that set forth above.

Whether or not the additional materials mentioned in the above embodiments are employed in combination with the essential starting materials it should be noted that the catalyst produced may be in solid form or liquid form depending upon the particular proportion of amine, hydrogen peroxide, and other optional starting materials when used, to molybdenum atoms reacted. In those instances where the catalyst formed is a solid, the catalyst will settle out, at least in part, upon cooling of the reaction mixture, and may be separated from the solvent by any known method, e.g., simple filtration. When the catalyst obtained is a liquid, the entire reaction product may be effectively used as a catalyst and no separation is necessary.

As mentioned, the molybdenum salt catalysts of the present invention are useful in the preparation of various organic epoxides produced by indirect oxidation in which a peroxidic compound is employed as the oxygen contributor. Alkylene compounds characterized by an olefinic unsaturation, i.e., having the functional group >C=C<, are oxidized to obtain the corresponding alkylene oxide. The term alkylene is used herein to include both substituted and unsubstituted compounds and encompasses any organic compound having an olefinic bond which may be oxidized with hydrogen peroxide in the presence of a metal compound catalyst. Among the alkylenes which may be oxidized by the catalysts of the present invention are ethylenic hydrocarbons having, for example, 2 to 10 carbon atoms, e.g., 3 to 6 carbon atoms. For example, ethylene, propylene, butene, hexene, etc. as well as polyethylenic hydrocarbons, such as butadiene or isoprene, and cyclic compounds such as cyclohexene or styrene may be epoxidized. Additionally, substituted compounds such as ethylenic alcohols, e.g., allyl alcohol, ethylenic halides, e.g., allyl chloride, as well as unsaturated oils and fats may be oxidized with the catalysts of the present invention.

The alkylene is preferably oxidized in the liquid phase although gaseous alkylene may be employed. When desired, elevated pressures may be used so as to maintain the alkylene material in the liquid phase. Generally, an appropriate solvent is used which is compatible with and inert to both the alkylene and the hydrogen peroxide. An organic solvent of a polar nature sufficient to obtain a homogeneous mixture with the alkylene and the hydrogen peroxide is preferred. The alcohols, especially the secondary alcohols, e.g., isopropanol and sec-butanol, as well as glycols, esters, e.g., isopropyl acetate, linear or cyclic ethers and a few weak carboxylic acids are preferred.

Typically, for the epoxidation reaction, the organic solvent may contain the hydrogen peroxide in solution, and this solution may be combined with the alkylene to produce a reaction solution. When this technique is employed, about 1 percent to about 50 percent or more preferably about 5 percent to about 30 percent of hydrogen peroxide is used based on the weight of the solvent. Also, in order to retard the co-production of undesirable organic compounds such as glycols, it is preferred to have no more than a minor amount of water present during oxidation. Because the oxidation of the alkylene produces water by-product, the hydrogen peroxide feed preferably contains less than 10 percent water, for example, less than 1 percent water, based on the weight of the epoxidation reaction feed.

The alkylene is generally reacted with the hydrogen peroxide in at least an equivalent amount based on the number of olefinic groups per molecule of alkylene to be oxidized. When the alkylene has only one olefinic bond, then at least an equimolar amount of it is used with the hydrogen peroxide, e.g., about 1 to about 5 moles, preferably about 1 to about 2 moles, of alkylene per mole of hydrogen peroxide is used. As mentioned, the oxidation of the alkylene is preferably carried out in the liquid phase and in a single solvent solution.

The hydrogen peroxide may be any commercially available product or it may be crude, e.g., produced on site by known methods. For example, solutions of hydrogen peroxide in isopropanol are obtained by oxidation of isopropanol with oxygen at elevated temperatures. In this case, the produced solution, after undesirable by-products such as acetone are at least partially removed, may be employed in the alkylene oxidation and the isopropanol will become the solvent for the alkylene oxidation reaction solution.

The molybdenum salt catalysts of the present invention are used to promote the alkylene oxidation and are soluble in reaction solutions such as those described above. Generally, the catalyst should be used in an effective amount to obtain commercially acceptable yields. An effective amount will vary depending upon the specific catalyst used, the particular alkylene compound or compounds being epoxidized and the reactor design and its flow through characteristics such as residence time. In general, about 0.027 to about 0.35 or so of gram-atoms of molybdenum per liter of reaction solution and preferably about 0.055 to about 0.17 grams-atoms are used. In other words it is desirable to have about 0.004 to about 0.05 moles of molybdenum per mole of alkylene compound, and preferably about 0.008 to about 0.025 moles, in the reaction solution, although more catalyst may be used without detrimentally affecting epoxidation.

The alkylene oxidation reaction employing a molybdenum salt catalyst of the present invention may be performed in a batch operation or it may be a continuous process. In either case the reaction will generally be completed to a commercially acceptable degree within a short period of time, and actual residence time will, as suggested, depend upon the particular reactor design and operating conditions employed. The alkylene oxidation reaction is generally carried out in the range of about 0°C. to about 80°C., and preferably about 20°C. to about 60°C., at a pressure sufficient to maintain the oxidation reaction solution in the liquid phase. The oxidation of the alkylene may be satisfactorily completed within a matter of minutes, or it may take days but is generally completed within about 5 hours, e.g., 2 or 3 hours, more or less.

During the oxidation reaction, the hydrogen peroxide gives up an oxygen atom to the alkylene to effect epoxidation. A product mixture of water, the alkylene oxide, the molybdenum salt catalyst and undesirable organic by-products is obtained. Because the water which is formed enhances the production of undesirable glycols, it is desirable to maintain the amount of water in the reaction mixture at a minimum. When a batch system is employed, the production of undesirable glycol may be mitigated by maintaining the total amount of water present at the end of the reaction below about 20 percent by weight based on the total weight of the reaction mixture. When a continuous system is used, water may be removed from the reaction mixture by removal of a portion of the reactants, separation of the water by evaporation techniques and recycle of the non-aqueous constituents, or alternatively the reaction mixture may have a sufficient amount of solvent so as to produce a low water content product mixture on a continuous basis.

The reaction product containing the desired alkylene oxide obtained by use of a catalyst of the present invention may be subjected to distillation or other separation technique and the usable constituents, e.g., unreacted alkylene, solvent, etc. and the molybdenum salt catalyst may be recovered and recycled to the system as desired. Also, the degree of purification of the alkylene oxide employed depends upon the ultimate utility of the alkylene oxide and is a matter of choice.

The following examples illustrate various embodiments of preparing and using the novel molybdenum salt catalysts of the present invention without limiting the scope of the present invention thereto:

EXAMPLE 1

A reactor having a heater, a reflux condenser and an agitator is charged with 660 grams (4.59 moles) of molybdenum trioxide and 2695 ml. of isopropanol to form a suspension. The suspension is stirred and heated to about 70°C. and 650 ml. of a 20% (±2%) solution of total peroxide (more than 85% hydrogen peroxide, remainder organic peroxides) in isopropanol (2.32 moles of $H_2O_2$) is added. Agitation is maintained and the reaction mixture is heated to reflux (about 80°C.). After refluxing for about 30 minutes, 154.79 grams (1.53 moles) of triethylamine is added stepwise over a period of about 35 minutes. The reaction mixture is refluxed for about 2 hours under agitation and then cooled to room temperature.

The reaction mixture is filtered and the residue is washed with isopropanol under suction to obtain a solid catalyst of the present invention. NMR and IR analysis suggest that a salt containing triethylammonium ions as well as some coordinated triethylamine is obtained. It is theorized that the major reaction which occurs in this example is represented by the following equation, although the specific catalyst obtained is not completely defined and should not be limited thereto:

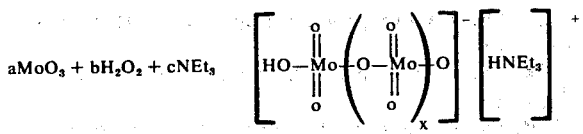

wherein $a$, $b$, and $c$ are equation balancing numbers and $x$ is an average number from 0 to 10.

EXAMPLE 2

The method of Example 1 is repeated except that an equimolar amount of triethylamine N-oxide is substituted for the triethylamine. An effective epoxidation catalyst is obtained which is similar to that obtained in Example 1 except that it is speculated that the cations comprise both $(HNEt_3)^+$ and $(HONEt_3)^+$.

EXAMPLE 3

20.00 Grams (0.1390 moles) of $MoO_3$, 71 ml. of a 20% (±2%) total peroxide in isopropanol solution (0.278 moles $H_2O_2$) and 7.51 grams (0.417 moles) of $H_2O$ are charged to a reactor vessel and are stirred and heated to reflux at about 80°C. About 7.03 grams (0.0695 moles) of triethylamine are added over a two minute period and then the reaction mixture is refluxed for about ten minutes and then cooled to room temperature to form a precipitate.

A green solid precipitate is collected via filtration and washed with isopropyl alcohol under suction. The solid reaction product is determined to be an effective epoxidation catalyst.

EXAMPLE 4

Example 3 is repeated except that diethylbutylamine is substituted for the triethyl amine in an equimolar amount. The reaction product is determined to be an effective epoxidation catalyst. It is theorized that anions present are diethylbutyl ammonium ions.

EXAMPLE 5

Example 3 is repeated except that the triethylamine is added in place of the hydrogen peroxide before initial reflux and then the hydrogen peroxide is added. The reaction product obtained is apparently the same as that produced in Example 3.

EXAMPLE 6

To a suitable reactor is added 20.00 grams (0.1390 moles) of $MoO_3$, 53 ml. of a 20% (±2%) solution of total peroxide in isopropanol (0.210 moles of $H_2O_2$), 50 ml. of isopropanol and 5.28 grams (0.0695 moles) of propylene glycol. The suspension is stirred and heated to reflux (80°C.) and then 14.06 grams (0.1390 moles) of triethylamine in 25 ml. of isopropanol is added step-wise over a 30 minute period. The reaction mixture is cooled and a solid catalyst is obtained by filtering the mixture under suction.

The resulting reaction product is found to be a useful catalyst for epoxidation reactions, especially for the epoxidation of propylene in a hydrogen peroxide-isopropanol medium.

EXAMPLE 7

20.00 Grams (0.1390 moles) of $MoO_3$, 142 ml. of a 20% (±2%) total peroxide in isopropanol solution (0.556 moles of $H_2O_2$) and 42.26 grams (0.556 moles) of propylene glycol are charged to a reactor and the contents are heated to reflux while being stirred. After reflux of the reaction mixture for about one-half hour, 9.37 grams (0.0926 moles) of triethylamine is added step-wise over a ten-minute period. The reaction mixture is then refluxed for 4 hours, after which the isopropanol is stripped from the mixture and an oily liquid catalyst is obtained and cooled.

EXAMPLE 8

A stainless steel pressure vessel is charged with 110 grams of 20% (±2%) solution of total peroxide in isopropanol (a total of 0.582 moles of $H_2O_2$) and 2.5 grams of the novel molybdenum salt catalyst by the method of Example 1 (corresponding to 0.013 moles of molybdenum). The pressure vessel is immersed in a 30°C. bath, and 42 grams (1 mole) of liquified propylene is then charged to the sealed pressure vessel at a pressure of about 140 psi. The epoxidation reaction mixture is stirred and maintained at 30°C. for about 4 hours.

Samples of the product mixture are analyzed and found to contain substantial amounts of propylene oxide.

EXAMPLE 9

Example 8 is repeated except that an equimolar amount of butylene is substituted for the propylene, and the reaction is carried out at atmospheric rather than at an elevated pressure. The product mixture is found to contain butylene oxide.

EXAMPLE 10

Example 8 is repeated except that the catalyst of Example 7 is used in place of the Example 1 catalyst. The reaction product mixture is found to obtain a substantial amount of propylene oxide.

I claim:

1. A method of preparing a molybdenum salt catalyst, comprising:
reacting at elevated refluxing temperatures an oxygen-containing molybdenum compound selected from the group consisting of molybdenum dioxide, molybdenum sesquioxide, molybdenum trioxide and the ammonium salt of molybdic acid, and mixtures thereof with about 0.1 to about 4 moles of hydrogen peroxide per mole of molybdenum and about 0.1 to about 4 moles of an amine per mole of molybdenum, the amine being (a) a compound of the formula $R_1R_2R_3N$ wherein $R_1$, $R_2$, and $R_3$ are each independently selected from hydrogen, unsubstituted alkyls having about 1 to about 10 carbon atoms, and unsubstituted aryls having about 6 to about 10 carbon atoms, with the proviso that at least one of $R_1$, $R_2$, and $R_3$ is not hydrogen, or (b) an N-oxide of a tertiary amine compound of the above formula.

2. The method of claim 1 wherein about 1 to about 50 moles of water are included as a reactant.

3. The method of claim 1 wherein about 0.1 to about 4 moles of an alkylene glycol are included as a reactant.

4. The method of claim 3 wherein the alkylene glycol has 2 to 6 carbon atoms.

5. The method of claim 4 wherein about 0.5 to about 2 moles of an alkylene glycol are included as a reactant.

6. The method of claim 1 wherein the $R_1$, $R_2$, and $R_3$ of the amine are each independently selected from unsubstituted alkyls having about 1 to about 6 carbon atoms.

7. The method of claim 6 wherein about 0.5 to about 2 moles of hydrogen peroxide and about 0.3 to about 2 moles of the amine are reacted per mole of molybdenum.

8. The method of claim 7 wherein about 1 to about 50 moles of water are included as a reactant.

9. The method of claim 7 wherein about 10 to about 20 moles of water are included as a reactant.

10. The method of claim 7 wherein about 0.1 to about 4 moles of an alkylene glycol are included as a reactant.

11. The method of claim 10 wherein the alkylene glycol has 2 to 6 carbon atoms.

12. The method of claim 11 wherein about 0.5 to about 2 moles of an alkylene glycol are included as a reactant.

13. The method of claim 7 wherein the reaction temperature is about 60°C. to about 100°C.

14. The method of claim 13 wherein the amine is a tertiary amine, or its N-oxide, in which $R_1$, $R_2$, and $R_3$ are each independently selected from methyl, ethyl and butyl.

15. The method of claim 14 wherein the amine is triethyl amine.

16. The method of claim 15 wherein the oxygen-containing molybdenum compound is molybdenum trioxide.

17. The reaction product prepared by the method of claim 1.

18. The reaction product prepared by the method of claim 2.

19. The reaction product prepared by the method of claim 3.

20. The reaction product prepared by the method of claim 4.

21. The reaction product prepared by the method of claim 5.

22. The reaction product prepared by the method of claim 6.

23. The reaction product prepared by the method of claim 7.

24. The reaction product prepared by the method of claim 8.

25. The reaction product prepared by the method of claim 9.

26. The reaction product prepared by the method of claim 10.

27. The reaction product prepared by the method of claim 11.

28. The reaction product prepared by the method of claim 12.

29. The reaction product prepared by the method of claim 13.

30. The reaction product prepared by the method of claim 14.

31. The reaction product prepared by the method of claim 15.

32. The reaction product prepared by the method of claim 16.

* * * * *

UNITED STATES PATENT OFFICE
CERTIFICATE OF CORRECTION

Patent No. 3,953,362     Dated April 27, 1976

Inventor(s) Ellwood L. Lines, John A. Herbst and Robert J. Fairbrother

It is certified that error appears in the above-identified patent and that said Letters Patent are hereby corrected as shown below:

Column 1, line 32, the word "sarting" should read --starting--.

Column 2, line 49, the word "aout" should read --about--.

Column 5, lines 37-41, the following equation should read

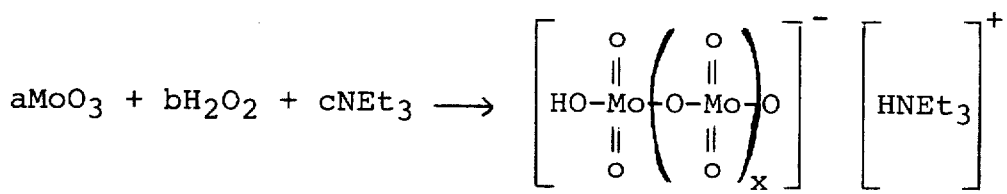

Column 7, line 7, "I claim" should read --WHAT IS CLAIMED IS--.

Signed and Sealed this

Twentieth Day of July 1976

[SEAL]

Attest:

RUTH C. MASON
*Attesting Officer*

C. MARSHALL DANN
*Commissioner of Patents and Trademarks*